United States Patent
Kanatani et al.

(10) Patent No.: US 7,790,731 B2
(45) Date of Patent: *Sep. 7, 2010

(54) CRYSTAL FORM OF 2-METHYL-3-{4-[3-(1-PYRROLIDINYL)PROPOXY]PHENYL}-5-TRIFLUOROMETHYL-4(3H)-QUINAZOLINONE

(75) Inventors: Akio Kanatani, Ushiku (JP); Nagaaki Sato, Tsukuba (JP); Tsuyoshi Nagase, Tsukuba (JP); Shigeru Tokita, Tsukuba (JP)

(73) Assignee: Banyu Pharmaceutical Co. Ltd., Tokyo (JP)

(*) Notice: Subject to any disclaimer, the term of this patent is extended or adjusted under 35 U.S.C. 154(b) by 79 days.

This patent is subject to a terminal disclaimer.

(21) Appl. No.: 11/884,138

(22) PCT Filed: Feb. 13, 2006

(86) PCT No.: PCT/JP2006/302900
§ 371 (c)(1),
(2), (4) Date: Aug. 9, 2007

(87) PCT Pub. No.: WO2006/085692
PCT Pub. Date: Aug. 17, 2006

(65) Prior Publication Data
US 2008/0139589 A1    Jun. 12, 2008

(30) Foreign Application Priority Data
Feb. 14, 2005    (JP)    ............... 2005-036659

(51) Int. Cl.
*A61K 31/517*    (2006.01)

(52) U.S. Cl. ............ 514/266.2; 544/290; 548/518

(58) Field of Classification Search ............. 514/266.2; 544/290; 548/518
See application file for complete search history.

(56) References Cited

U.S. PATENT DOCUMENTS

| 5,948,775 A | 9/1999 | Koko et al. |
| 2005/0059651 A1 | 3/2005 | Armstrong et al. |
| 2005/0182045 A1 | 8/2005 | Nagase et al. |

FOREIGN PATENT DOCUMENTS

DE    1939109    3/1970

OTHER PUBLICATIONS

Daleva L et al., Database CAPLUS on STN, AN 1973:427214, DN 79:27214, Pharmacological Study of a Gropup of Quinazolinone Derivatives II. Trudove na Nauchnoizsledovatelskiya Khimikofarmatsevichen Institut, 1972, No. 7, pp. 241-252.
R. Leurs et al., "Therapetuic Potential of Histamine H3 Receptor Agonists and Antagonists", *Trends in Pharmacological Science*, 1998, vol. 19, pp. 177-183.
P. J. Barnes, "Airway Neuropeptides and Asthma", *Trends in Pharmacological Science*, 1987, vol. 8, pp. 24-27.
R. E. Brown et al., "The Physiology of Brain Histamine" *Progress in Neurobiology*, 2001, vol. 63, pp. 637-632
J. C. Schwartz, Histamine as a Transmitter in Brain, *Life Sciences*, 1975, vol. 17, pp. 503-518.
T. W. Lovenberg et al., "Cloning and Functional Expression of the Human Histamine H3 Receptor", *Molecular Pharmacology*, 1999, vol. 55, pp. 1101-1107.

*Primary Examiner*—James O Wilson
*Assistant Examiner*—Douglas M Willis
(74) *Attorney, Agent, or Firm*—J. Eric Thies; Gerard M. Devlin (57) ABSTRACT

The present invention is directed to a form I crystal of 2-methyl 3-{4-[3-(1-pyrrolidinyl)propoxy]phenyl}-5-trifluoromethyl-4(3H)-quinazolinone that is useful for example in the treatment of sleep disorders or various sleep disorder-associated diseases.

13 Claims, 1 Drawing Sheet

Fig. 1

CRYSTAL FORM OF 2-METHYL-3-{4-[3-(1-PYRROLIDINYL)PROPOXY]PHENYL}-5-TRIFLUOROMETHYL-4(3H)-QUINAZOLINONE

CROSS-REFERENCE TO RELATED APPLICATIONS

This application is a U.S. National Phase application under 35 U.S.C. §371 of PCT Application No. PCT/JP2006/302900, filed Feb. 13, 2006, which claims priority under 35 U.S.C. §119 from JP Application No. JP2005-36659, filed Feb. 14, 2005.

STATEMENT REGARDING FEDERALLY SPONSORED RESEARCH OR DEVELOPMENT

Not applicable

THE NAMES OF THE PARTIES TO A JOINT RESEARCH AGREEMENT

Not applicable

INCORPORATION-BY-REFERENCE OF MATERIAL SUBMITTED ON A COMPACT DISK

Not applicable

BACKGROUND OF THE INVENTION (1) Field of the Invention

The present invention relates to a crystal of a 4(3H)-quinazolinone derivative, more precisely to a form I crystal of 2-methyl-3-{4-[3-(1-pyrrolidinyl)propoxy]phenyl}-5-trifluoromethyl-4(3H)-quinazolinone.

(2) Description of Related Art

It has been known that, in organisms such as typically mammals, histamine that is a physiologically-active endogenous factor functions as a neurotransmitter and has extensive pharmacological activities (for example, see Non-Patent Reference 1).

Immunohistochemical studies have made it clear that a histamine-agonistic (producing) cell body exists in the nodal papillary nucleus in a posterior hypothalamic region and that histamine nerve fibers project in an extremely broad range in a brain, which supports various pharmacological effects of histamine (for example, see Non-Patent Reference 2). The existence of histamine-agonistic nerves in the nodal papillary nucleus in a posterior hypothalamic region suggests that histamine may have an important role in control of physiological functions relating to brain functions, especially to hypothalamic functions (sleep, vigilance rhythm, incretion, eating and drinking behavior, sexual action, etc.) (for example, see Non-Patent Reference 3).

The existence of the projection in the brain region that relates to vigilance sustenance, for example, in a cerebral cortex suggests the role in regulation of vigilance or vigilance-sleep cycle. The existence of the projection in many peripheral structures such as hippocampus and amygdaloid complex suggests the role in regulation of autonomic nerves, emotion, control of motivated action and learning/memory process.

When released from producing cells, histamine reacts with a specific polymer that is referred to as a receptor on the surface of a cell membrane or inside a target cell, therefore exhibiting its pharmacological effects for regulation of various body functions. Heretofore, four types of histamine receptors have been found. In particular, the presence of a histamine receptor that participates in the central and peripheral nervous functions, a histamine-H3 receptor, has been shown by various pharmacological and physiological studies (for example, see Non-Patent Reference 4). Recently, human and rodent histamine-H3 receptor genes have been identified and their existence has been revealed (for example, see Non-Patent Reference 5).

It is shown that the histamine-H3 receptor exists in the presynaptic membrane of central or peripheral neurocytes and functions as a self-receptor, therefore controlling the release of histamine and controlling even the release of other neurotransmitters. Specifically, it is reported that a histamine-H3 receptor agonist, or its antagonist or inverse-agonist regulates the release of histamine, noradrenaline, serotonin, acetylcholine or dopamine from nerve terminal. For example, the release of these neurotransmitters is inhibited by an agonist such as (R)-(α)-methylhistamine, and is promoted by an antagonist or inverse-agonist such as thioperamide (for example, see Non-Patent Reference 6).

Patent Reference 1: German Patent 1,939,109,
Patent Reference 2: U.S. Pat. No. 5,948,775,
Non-Patent Reference 1: *Life Science*, Vol. 17, p. 503 (1975),
Non-Patent Reference 2: *Journal of Comprehensive Neurology*, Vol. 273, p. 283,
Non-Patent Reference 3: *Progress in Neurobiology*, Vol. 63, p. 637 (2001),
Non-Patent Reference 4: *Trends in Pharmacological Science*, Vol. 8, p. 24 (1986),
Non-Patent Reference 5: *Molecular Pharmacology*, Vol. 55, p. 1101 (1999),
Non-Patent Reference 6: *Trends in Pharmacological Science*, Vol. 19, p. 177 (1998).

BRIEF SUMMARY OF THE INVENTION

An object of the invention is to provide a substance having an effect of inhibiting histamine from binding to a histamine-H3 receptor or an effect of inhibiting the homeostatic activity that a histamine-H3 receptor has, or that is, a substance capable of effectively functioning as a histamine-H3 receptor antagonist or inverse-agonist when taken in living bodies.

In order to attain the above-mentioned object, the invention provides a crystal of 2-methyl-3-{4-[3-(1-pyrrolidinyl)propoxy]phenyl}-5-trifluoromethyl-4(3H)-quinazolinone (hereinafter this may be referred to as "form I crystal").

The form I crystal typically has, in powdery X-ray diffractiometry, peaks at diffraction angles (2θ±0.2°) of 6.4°, 9.7°, 20.3° and 20.6°, more precisely, in powdery X-ray diffractiometry, peaks at diffraction angles (2θ±0.2°) of 6.4°, 9.7°, 12.9°, 14.7°, 19.5°, 20.3°, 20.6°, 21.2° and 26.7°, even more precisely, in powdery X-ray diffractiometry, peaks at diffraction angles (2θ±0.2°) of 6.4°, 9.7°, 10.2°, 12.9°, 14.2°, 14.7°, 16.0°, 16.3°, 16.8°, 17.6°, 19.5°, 20.3°, 20.6°, 21.2°, 21.8°, 22.1°, 22.4°, 22.6°, 24.0°, 24.3°, 24.9°, 25.7°, 25.9°, 26.5°, 26.7°, 27.4°, 29.1°, 29.4°, 32.3° and 39.0°.

Typically, the form I crystal has, in powdery X-ray diffractiometry, strong peaks at diffraction angles (2θ±0.2°) of 6.4°, 9.7°, 20.3° and 20.6°, and has medium peaks at diffraction angles (2θ±0.2°) of 12.9°, 14.7°, 19.5°, 21.2° and 26.7°. Preferably, it has, in powdery X-ray diffractiometry, the diffraction pattern shown in FIG. 1 or a diffraction pattern crystallographically equivalent to it.

In general, the form I crystal has, in differential scanning colorimetry, an endothermic peak at 141° C., and may be produced by reacting a compound of the following formula (a) with a compound of the following formula (b) or its acid-addition salt.

The above-mentioned form I crystal of 2-methyl-3-{4-[3-(1-pyrrolidinyl)propoxy]phenyl}-5-trifluoromethyl-4(3H)-quinazolinone is a novel crystal form of the compound, 2-methyl-3-{4-[3-(1-pyrrolidinyl)propoxy]phenyl}-5-trifluoromethyl-4(3H)-quinazolinone disclosed in WO2005/077905, which has been found in the process of producing the compound; and this has an effect of inhibiting histamine from binding to a histamine-H3 receptor or an effect of inhibiting the homeostatic activity that a histamine-H3 receptor has, and, when taken in living bodies, this effectively functions as a histamine-H3 receptor antagonist or inverse-agonist.

The form I crystal has properties (stability, etc.) favorable for a process of its industrial-scale production, for example, for a process of formulating it into pharmaceutical preparations. Further, as compared with amorphous 2-methyl-3-{4-[3-(1-pyrrolidinyl)propoxy]phenyl}-5-trifluoromethyl-4(3H)-quinazolinone, the form I crystal has excellent thermal stability and light stability.

Recent studies have shown that a histamine-H3 receptor has extremely high homeostatic activities (activities observed in the absence of an endogenous agonistic factor, e.g., histamine) in the receptor-expressing cells/tissues or in a membrane fraction derived from the expressing cells/tissues and even in living bodies (for example, *Nature*, Vol. 408, p. 860). It is reported that these homeostatic activities are inhibited by an inverse-agonist. For example, thioperamide or syproxyfan inhibits the homeostatic self-receptor activity of a histamine H3 receptor, and, as a result, promotes the release of neurotransmitters, for example, release and liberation of histamine from nerve terminal.

In animal experiments with rats, a high-level selective inhibitor of histamine synthase (histidine decarboxylase) inhibits the vigilance of rats, and therefore it is shown that histamine participates in regulating motive vigilance. Regarding cats, administration of a histamine-H3 receptor agonist, (R)-(α)-methylhistamine to cats increases their deep slow-wave sleep (for example, *Brain Research*, Vol. 523, p. 325 (1990)).

Contrary to this, a histamine-H3 receptor antagonist or inverse-agonist, thioperamide dose-dependently increases vigilance. In addition, thioperamide decreases slow-wave and REM sleep (*Life Science*, Vol. 48, p. 2397 (1991)). A histamine-H3 receptor antagonist or inverse-agonist, thioperamide or GT-2331 reduces emotional cataplexy and sleep of narcoleptic dogs (for example, *Brain Research*, Vol. 793, p. 279 (1998)).

These informations suggest that the H3 receptor may participate in regulation of vigilance-sleep and in sleep disorder-associated diseases, further suggesting a possibility that a selective histamine-H3 agonist, antagonist or inverse-agonist may be useful for treatment of sleep disorders or various sleep disorder-associated diseases (for example, idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, schizophrenia). Accordingly, the form I crystal of the invention may be used for treatment of these disorders.

On the other hand, in animal experiments with rats, the administration of a histamine-H3 receptor antagonist or inverse-agonist, thioperamide or GT-2331 relieves the condition of learning disorder (LD) and attention deficit hyperactivity disorder (ADHD) (for example, *Life Science*, Vol. 69, p. 469 (2001)); and therefore, it may be said that the selective 143 agonist or antagonist or inverse-agonist may be useful for treatment and/or prevention of learning disorder or attention deficit hyperactivity disorder. Accordingly, the form I crystal of the invention is highly useful for treatment and prevention of these disorders.

In animal experiments with rats, administration of histamine to their ventricle of brain inhibits their eating behavior, therefore suggesting that histamine may participate in regulation of eating behavior (for example, *Journal of Physiology and Pharmacology*, Vol. 49, p. 191 (1998)). A histamine-H3 receptor antagonist or inverse-agonist, thioperamide dose-dependently inhibits eating behavior. In addition, thioperamide promotes intracerebral histamine release (for example, *Behavioural Brain Research*, Vol. 104, p. 147 (1999)).

These informations suggest that a histamine H3 receptor may participate in eating behavior regulation, further suggesting that a histamine-H3 antagonist or inverse-agonist may be useful for prevention or treatment of metabolic system diseases such as eating disorder, obesity, diabetes, emaciation, hyperlipemia. Accordingly, the form I crystal of the invention is useful as a preventive or remedy for these disorders.

In animal experiments with rats, a histamine-H3 receptor agonist, (R)-(α)-methylhistamine dose-dependently lowers their basal diastolic pressure, and its action is antagonized by a histamine-H3 receptor antagonist or inverse-agonist, thioperamide (for example, *European Journal of Pharmacology*, Vol. 234, p. 129, (1993)).

These informations suggest that a histamine-H3 receptor may participate in regulation of blood pressure, heart beat and cardiac output, further suggesting that a histamine-H3 receptor agonist, antagonist or inverse-agonist may be useful for prevention or treatment of circulatory system diseases such as hypertension and various cardiac disorders. Accordingly, the form I crystal of the invention is highly useful for treatment and prevention of these disorders.

In animal experiments with rats, administration of a histamine-H3 receptor agonist, (R)-(α)-methylhistamine lowers their object cognitive and learning effects in the object cognition test and the passive turnout test with them. On the other hand, in a scopolamine-induced amnesia test, a histamine-H3 receptor antagonist or inverse-agonist, thioperamide dose-dependently relieves amnesia induced by this reagent (for example, *Pharmacology, Biochemistry and Behavior*, Vol. 68, p. 735 (2001)).

These informations suggest a possibility that a histamine-H3 receptor antagonist or inverse-agonist may be useful for prevention or treatment of various diseases accompanied by memory/learning disorder, for example, Alzheimer's disease, Parkinson's disease or attention deficit/hyperactivity disorder. Accordingly, the form I crystal of the invention is highly useful for treatment and prevention of these disorders.

In animal experiments with mice, a histamine-H3 receptor antagonist or inverse-agonist, thioperamide dose-dependently inhibits the spasm induced by electric shock or the epileptoid seizure induced by pentylene tetrazole (PTZ) (for example, *European Journal of Pharmacology*, Vol. 234, p. 129 (1993), and *Pharmacology, Biochemistry and Behavior*, Vol. 68, p. 735 (2001)).

These informations suggest that a histamine-H3 receptor antagonist or inverse-agonist may be useful for prevention or treatment of epilepsy or central spasm. Accordingly, the form I crystal of the invention is highly useful for treatment and prevention of these disorders.

Accordingly, the invention provides the form I crystal functioning as a histamine-H3 receptor antagonist and the form I crystal functioning as a histamine-H3 receptor inverse-agonist when taken in living bodies. The invention also provides a preventive or remedy for metabolic system diseases, circulatory system diseases or nervous system diseases, which contains the above-mentioned form I crystal as the active ingredient thereof.

The metabolic system diseases are at least one selected from obesity, diabetes, hormone secretion disorder, hyperlipemia, gout and fatty liver; the circulatory system diseases are at least one selected from stenocardia, acute/congestive cardiac insufficiency, cardiac infarction, coronary arteriosclerosis, hypertension, nephropathy and electrolyte disorder.

The nervous system diseases are at least one selected from sleep disorder, diseases accompanied by sleep disorder, bulimia, emotional disorder, epilepsy, delirium, dementia, attention deficit/hyperactivity disorder, memory disorder, Alzheimer's disease, Parkinson's disease, cognition disorder, motion disorder, paresthesia, dysosmia, morphine resistance, drug dependency, alcoholism and tremor.

The nervous system diseases are at least one selected from idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, anxiety and schizophrenia.

The form I crystal may be used, as combined with co-drugs. Accordingly, the invention further provides a preventive or remedy for metabolic system diseases, circulator system diseases or nervous system diseases, which contains the form I crystal and a co-drug, as the active ingredients thereof. The co-drug includes a remedy for hyperlipemia, a remedy for diabetes, a remedy for hypertension, an anti-obesity drug.

DETAILED DESCRIPTION OF THE INVENTION

The form I crystal of the invention is a novel crystal form of 2-methyl-3-{4-[3-(1-pyrrolidinyl)propoxy]phenyl}-5-trifluoromethyl-4(3H)-quinazolinone, found in a process of producing the compound.

In an embodiment of the invention, the powdery X-ray diffractiometric result of the form I crystal is as in Table 1 below, and the concrete data of the relative intensity of the substance are shown in Table 2. Powdery X-ray diffractiometry may give an error of ±0.2°, and therefore in the invention, the position of the diffraction peak is defined as "having a diffraction peak at a diffraction angle (2θ±0.2°) of A°". The expression "at a diffraction angle (2θ±0.2°) of A°" means that the analyzed substance has a diffraction peak at a diffraction angle (2θ) of from (A−0.2)° to (A+0.2)°.

TABLE 1

| 2θ ± 0.2° | Relative Intensity |
|---|---|
| 6.4 | strong |
| 9.7 | strong |
| 10.2 | weak |
| 12.9 | moderate |
| 14.2 | weak |
| 14.7 | moderate |
| 16.0 | moderate to weak |
| 16.3 | moderate to weak |
| 16.8 | weak |
| 17.6 | weak |
| 19.5 | moderate |
| 20.3 | strong |
| 20.6 | strong |
| 21.2 | moderate |
| 21.8 | weak |
| 22.1 | moderate to weak |
| 22.4 | weak |
| 22.6 | weak |
| 24.0 | moderate to weak |
| 24.3 | moderate to weak |
| 24.9 | weak |
| 25.7 | weak |
| 25.9 | weak |
| 26.5 | weak |
| 26.7 | moderate |
| 27.4 | weak |
| 29.1 | weak |
| 29.4 | weak |
| 32.3 | weak |
| 39.0 | weak |

TABLE 2

| 2θ ± 0.2° | Relative Intensity [cps] |
|---|---|
| 6.4 | 100.0 |
| 9.7 | 34.0 |
| 10.2 | 2.1 |
| 12.9 | 10.3 |
| 14.2 | 2.5 |
| 14.7 | 14.5 |
| 16.0 | 4.9 |
| 16.3 | 4.4 |
| 16.8 | 2.0 |
| 17.6 | 1.9 |
| 19.5 | 13.2 |
| 20.3 | 37.8 |
| 20.6 | 25.3 |
| 21.2 | 9.1 |
| 21.8 | 0.7 |
| 22.1 | 4.4 |
| 22.4 | 2.6 |
| 22.6 | 1.7 |
| 24.0 | 4.4 |
| 24.3 | 4.9 |
| 24.9 | 1.0 |
| 25.7 | 1.8 |
| 25.9 | 2.6 |
| 26.5 | 2.5 |
| 26.7 | 8.6 |
| 27.4 | 1.6 |
| 29.1 | 1.8 |

TABLE 2-continued

| 2θ ± 0.2° | Relative Intensity [cps] |
|---|---|
| 29.4 | 1.5 |
| 32.3 | 1.6 |
| 39.0 | 0.7 |

The form I crystal as above has an endothermic peak at 141° C. in differential scanning calorimetry (device: Perkin Elmer Diamond DSC, sample amount: 1.288 mg, sample cell: aluminium cell, flow: $N_2$, heating speed: 5° C./min, heat capacity: 80.69 J/g).

Method for Producing Form I Crystal

The form I crystal may be favorably produced according to a production method that comprises the following step 1 to step 5, in which the reaction scheme of the steps is as in the following chemical formula:

Scheme 1:

(Step 1)

This step is to produce a compound 2 (this is the same as the compound (a) mentioned in the above) by reacting a compound 1 with acetic anhydride. The amount of acetic anhydride to be used may be generally from 1 to 10 equivalents, preferably from 2 to 5 equivalents, relative to 1 equivalent of the compound 1. The reaction temperature may be from room temperature to 150° C., preferably from 100 to 130° C.; and the reaction time may be generally from 1 to 24 hours, preferably from 1 to 6 hours.

Not specifically defined, the reaction solvent to be used in this step may be any one not interfering with the reaction. For example, usable is dimethylformamide, dimethylsulfoxide, 1,4-dioxane, toluene or their mixed solvent; or acetic anhydride alone may be used.

Thus obtained, the compound 2 may be isolated and purified in any known separation and purification method of, for example, concentration, concentration in vacuo, solvent extraction, crystallization, re-precipitation, chromatography and the like; or not isolated and purified, it may be subjected to the next step.

(Step 2)

This step is to produce (3-hydroxypropyl)pyrrolidine by reacting 3-bromopropanol and pyrrolidine in the presence of a base. The base to be used in this step is, for example, sodium hydrogencarbonate, sodium carbonate, potassium carbonate, sodium hydride and the like. Of those, preferred are sodium carbonate and potassium carbonate. The amount of the base to be used may be generally from 1 to 10 equivalents, preferably from 2 to 5 equivalents relative to 1 equivalent of 3-bromopropanol.

In this step, potassium iodide, tetra-n-butylammonium iodide and the like may be present in the reaction system for the purpose of increasing the reactivity of 3-bromopropanol.

The amount of potassium iodide and the like to be used may be generally from 0.1 to 10 equivalents, preferably from 0.1 to 3 equivalents relative to 1 equivalent of 3-bromopropanol. The reaction temperature may be generally from 0° C. to 150° C., preferably from 50° C. to 100° C. The reaction time may be generally from 1 to 48 hours, preferably from 1 to 12 hours. Not specifically defined, the reaction solvent to be used in this step may be any one not interfering with the reaction. For example, usable is an inert solvent such as dimethylformamide, tetrahydrofuran (THF), 1,4-dioxane, acetone, methyl ethyl ketone and the like.

Thus obtained, (3-hydroxypropyl)pyrrolidine may be isolated and purified in any known separation and purification method of, for example, concentration, concentration in vacuo, solvent extraction, crystallization, re-precipitation, chromatography and the like; or not isolated and purified, it may be subjected to the next step.

(Step 3)

This step is to produce a compound 3 by reacting (3-hydroxypropyl)pyrrolidine and 4-fluoronitrobenzene in the presence of a base.

In this step, the base to be used is, for example, sodium hydride and the like. The amount of the base to be used may be generally from 1 to 10 equivalents, preferably from 1 to 5 equivalents relative to 1 equivalent of (3-hydroxypropyl)pyrrolidine. The amount of (3-hydroxypropyl)pyrrolidine to be used may be generally from 1 to 10 equivalents, preferably from 2 to 5 equivalents relative to 1 equivalent of 4-fluoronitrobenzene.

In this step, potassium iodide, tetra-n-butylammonium iodide and the like is preferably present in the reaction system for increasing the reactivity of 4-fluoronitrobenzene. The amount of potassium iodide and the like to be used may be generally from 0.1 to 10 equivalents, preferably from 0.1 to 3 equivalents.

The reaction temperature may be generally from 0° C. to 150° C., preferably from 50° C. to 100° C.; and the reaction time may be generally from 1 to 48 hours, preferably from 1 to 12 hours. The reaction solvent to be used in this step may be any one not interfering with the reaction. Preferred is an inert solvent such as dimethylformamide, tetrahydrofuran, 1,4-dioxane, acetone, methyl ethyl ketone and the like.

Thus obtained, the compound 3 may be isolated and purified in any known separation and purification method of, for example, concentration, concentration in vacuo, solvent extraction, crystallization, re-precipitation, chromatography and the like; or not isolated and purified, it may be subjected to the next step.

(Step 4)

This step is to produce a compound 4 (this is the same as the compound (b) mentioned in the above) through catalytic reduction of the compound 3 with a catalyst of palladium-carbon.

The amount of palladium-carbon to be used in this step may be generally from 0.01 to 1 equivalent, preferably from 0.05 to 0.5 equivalents relative to 1 equivalent of the compound 3. An acid such as p-toluenesulfonic acid monohydrate and the like may be added to the reaction system. The amount of the acid such as p-toluenesulfonic acid to be used may be generally from 0.1 to 10 equivalents, preferably from 1 to 3 equivalents relative to 1 equivalent of the compound 3. The reaction temperature may be generally from 0° C. to 80° C.; and the reaction time may be generally from 1 hour to 48 hours, preferably from 1 to 12 hours.

Thus obtained, the compound 4 may be isolated and purified in any known separation and purification method of, for example, concentration, concentration in vacuo, solvent extraction, crystallization, re-precipitation, chromatography and the like; or not isolated and purified, it may be subjected to the next step.

(Step 5)

This step is to produce a compound 5 of the invention, or that is, a form I crystal of 2-methyl-3-{4-[3-(1-pyrrolidinyl)propoxy]phenyl}-5-trifluoromethyl-4(3H)-quinazolinone, by reacting the compound 2 and the compound 4.

The amount of the compound 4 to be used in this step may be generally from 1 to 10 equivalents, preferably from 1 to 5 equivalents relative to 1 equivalent of the compound 2. The compound 4 may be not only tosylate but also, for example, any other acid addition salt such as hydrochloride, trifluoroacetate and the like, or may also be a free compound.

The reaction temperature may be generally from 20° C. to 180° C., preferably from 0° C. to 130° C.; and the reaction time may be generally from 1 to 72 hours, preferably from 3 hours to 12 hours.

Not specifically defined, the reaction solvent may be any one not interfering with the reaction. For example, usable are dimethylformamide, dimethylsulfoxide, acetic acid, 1,4-dioxane, toluene and the like. Of those, preferred are dimethylformamide, acetic acid and the like.

Thus obtained, the compound may be isolated and purified in any known separation and purification method of, for example, concentration, concentration in vacuo, solvent extraction, crystallization, re-precipitation, chromatography and the like. Preferably, the residue obtained through evaporation of the solvent is diluted with ethyl acetate, ether, chloroform and the like, preferably with ethyl acetate; and then this is poured into saturated citric acid, and the aqueous layer is washed with ethyl acetate, ether, chloroform and the like, preferably with ethyl acetate. Next, the pH of the aqueous layer is adjusted to be from 9 to 12, preferably from 10 to 11, for example, with sodium hydroxide, and then this is washed with ethyl acetate, ether, chloroform and the like, preferably with ethyl acetate. After the solvent was evaporated off, the obtained solid is recrystallized, for example, from ethyl acetate/n-heptane or ethanol/water.

Pharmaceutical Preparation Containing Form I Crystal

The form I crystal of 2-methyl-3-{4-[3-(1-pyrrolidinyl)propoxy]phenyl}-5-trifluoromethyl-4(3H)-quinazolinone of the invention may be used as an active ingredient of a preventive or remedy for metabolic system disorders, circulatory system disorders or nervous system disorders.

In case where the form I crystal is administered to humans, it may be administered orally or parenterally, and it may be formulated into pharmaceutical preparations suitable to such administration. Accordingly, the invention also provides a form I crystal of 2-methyl-3-{4-[3-(1-pyrrolidinyl)propoxy]phenyl}-5-trifluoromethyl-4(3H)-quinazolinone which has been formulated into pharmaceutical preparations suitable for oral or parenteral administration, according to a known formulation method.

In clinical use of form I crystal of the invention, pharmaceutically-acceptable additives may be added thereto to formulate various preparations in accordance with the intended administration route thereof. Various additives generally used in the field of pharmaceutical compositions may be used herein, including, for example, gelatin, lactose, white sugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin or hydroxypropylcyclodextrin and the like.

Combined with such additives, the compound of the invention may be formulated into solid preparations such as tablets, capsules, granules, powders or suppositories and the like, and liquid preparations such as syrups, elixirs or injections and the like. These preparations can be produced in any method known in the filed of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The preparations may contain the form I crystal of the invention in an amount of from 1.0 to 100% by weight, preferably from 1.0 to 60% by weight of the preparation. Formulation Examples are given below.

Formulation Example 1

10 parts of the form I crystal of the invention, 15 parts of heavy magnesium oxide and 75 parts of lactose are uniformly mixed to prepare a powdery or granular preparation having a particle size of at most 350 μm. The preparation is encapsulated to give capsules.

Formulation Example 2

45 parts of the form I crystal of the invention, 15 parts of starch, 16 parts of lactose, 21 parts of crystalline cellulose, 3 parts of polyvinyl alcohol and 30 parts of distilled water are uniformly mixed, then ground, granulated and dried, and then sieved to give a granular preparation having a particle diameter of from 1410 to 177 μm.

Formulation Example 3

A granular preparation is prepared in the same manner as in Formulation Example 2. 96 parts of the granular preparation is mixed with 3 parts of calcium stearate, and shaped under compression into tablets having a diameter of 10 mm.

Formulation Example 4

90 parts of the granular preparation obtained according to the method of Formulation Example 2 is mixed with 10 parts of crystalline cellulose and 3 parts of calcium stearate, and shaped under compression into tablets having a diameter of 8 mm. These are coated with a mixed suspension of syrup gelatin and precipitated calcium carbonate to give sugar-coated tablets.

These preparations may contain any other therapeutically-effective drug.

In its use, the form I crystal of the invention may be combined with any other drug effective for treatment of metabolic disorders and/or eating disorders. The individual ingredients to be combined may be administered at different times or at the same time, either as one preparation or as divided different preparations during the treatment. Accordingly, it should be so interpreted that the invention encompasses any administration at the same time or at different times, and the administration as referred to in the invention should be so interpreted. The combination of the form I crystal of the invention with any other drug effective for treatment of metabolic disorders and/or eating disorders includes, in principle, combinations thereof with any pharmaceutical preparation useful for treatment of metabolic disorders and/or eating disorders.

The form I crystal of the invention may also be combined with any other drug effective for hypertension, obesity-related hypertension, hypertension-related disorders, cardiomegaly, left ventricle hypertrophy, metabolic disorders, obesity, obesity-related disorders and the like (these are hereinafter referred to as "co-drugs"). Such co-drugs may be administered at the same time or at different times or successively in order in prevention or treatment of the above-mentioned disorders. When the form I crystal of the invention is used simultaneously with one or more co-drugs, then it may be in a pharmaceutical composition for one-dose administration. However, in such combination therapy, the composition containing the compound of the invention and the co-drug may be administered to subjects simultaneously, or separately or successively in separate packages. The composition and the co-drug may be packed separately. They may be administered at different times.

The dose of the co-drug may depend on the clinical use thereof, and may be suitably determined in accordance with the administration subject, the administration route, the diseases and the combination. The form of the co-drug for administration is not specifically defined, and it may be combined with the compound of the invention when they are administered. The administration mode includes, for example, the following: (1) The form I crystal of the invention is combined with a co-drug for simultaneous formulation to give a single preparation for single administration; (2) the form I crystal of the invention and a co-drug are separately formulated into different two preparations, and the two preparations are simultaneously administered in one administration route; (3) the form I crystal of the invention and a co-drug are separately formulated into different two preparations, and they are administered at different times in one and the same administration route; (4) the form I crystal of the invention and a co-drug are separately formulated into different two preparations, and they are administered at the same time in two different administration routes; (5) the form I crystal of the invention and a co-drug are separately formulated into different two preparations, and they are administered at different times in different administration routes (for example, the form I crystal of the invention and a co-drug are administered in that order, or in an order contrary to this).

The blend ratio of the form I crystal of the invention and the co-drug may be suitably determined depending on the administration subject, the administration route, and the disease for the administration.

The co-drugs usable in the invention include, for example "remedy for diabetes", "remedy for hyperlipemia", "remedy for hypertension", and "anti-obesity drugs" and the like. Two or more such co-drugs may be combined in any desired ratio.

The "remedy for diabetes" include, for example, the following:
1) PPAR-γ agonists such as glitazones [e.g., ciglitazone, darglitazone, englitazone, isaglitazone, (MCC-555)], pioglitazone, rosiglitazone, troglitazone, BRL49653, CLX-0921, 5-BTZD, GW-0207, LG-100641, LY-300512 and the like;
2) biguanides such as metformin, buformin, phenformin and the like;
3) protein tyrosine phosphatase 1B inhibitors;
4) sulfonylureas such as acetohexamide, chloropropamide, diabinese, glibenclamide, glipizide, glyburide, glimepiride, gliclazide, glipentide, gliquidone, glisolamide, tolazamide, tolbutamide and the like;
5) meglitinides such as repaglinide, nateglinide and the like;
6) α-glucoside hydroxylase inhibitors such as acarbose, adiposine, camiglibose, emiglitate, miglitol, voglibose, pradimicin-Q, salbostatin, CKD-711, MDL-25,673, MDL-73,945, MOR14 and the like;
7) α-amylase inhibitors such as tendamistat, trestatin, A13688 and the like;
8) insulin secretion promoters such as linogliride, A-4166 and the like;
9) fatty acid oxidation inhibitors such as clomoxir, etomoxir and the like;
10) A2 antagonists such as midaglizole, isaglidole, deriglidole, idazoxan, earoxan, fluparoxan and the like;
11) insulin or insulin mimetics such as biota, LP-100, novalapid, insulin detemir, insulin lispro, insulin glargine, insulin zinc, Lys-Pro-insulin, GLP-1 (73-7), GLP1 amide (7-36) and the like;

12) non-thiazolidinediones such as JT-501, farglitazar and the like; and
13) PPARα/γ dual-agonists such as CLX-0940, GW-1536, GW-1929, GW-2433, KRP-297, L-796449, LR-90, SB219994 and the like.

The "remedy for hyperlipemia" include, for example, the following:
1) bile acid absorption promoters such as cholesterylamine, colesevelem, colestipol, crosslinked dextran dialkylaminoalkyl derivatives, Colestid®, LoCholest®, Questran® and the like;
2) HMG-CoA reductase inhibitors such as atorvastatin, itavastatin, fluvastatin, lovastatin, pravastatin, rivastatin, rosuvastatin, simvastatin, ZD-4522 and the like;
3) HMG-CoA synthase inhibitors;
4) cholesterol absorption inhibitors such as snatol ester, β-sitosterol, sterol glucoside, ezetimibe and the like;
5) acyl-coenzyme A•cholesterol acyltransacylase inhibitors such as avasimibe, eflucimibe, KY-505, SMP-709 and the like;
6) CETP inhibitors such as JTT705, torcetrapib, CP532632, BAY-63-2149, SC-591, SC-795 and the like;
7) squalane synthetase inhibitors;
8) antioxidants such as probucol and the like;
9) PPARα agonists such as beclofibrate, benzafibrate, syprofibrate, clofibrate, etofibrate, fenofibrate, gemcabene, gemfibrozil, GW-7647, BM-170744, LY-518674, fibric acid derivatives (e.g., Atromid®, Lopid®, Tricor®) and the like;
10) FXR receptor antagonists such as GW-4064, SR-103912 and the like;
11) LXR receptor agonists such as GW3965, T9013137, XTCO-179628 and the like;
12) lipoprotein synthesis inhibitors such as niacin and the like;
13) renin-angiotensin system inhibitors;
14) microsomal triglyceride transportation inhibitors;
15) bile acid resorption inhibitors such as BARA1453, SC435, PHA384640, S-435, AZD7706 and the like;
16) PPARδ agonists such as GW501516, GW590735 and the like;
17) triglyceride synthesis inhibitors;
18) MTTP inhibitors such as LAB687, CP346086 and the like;
19) low-density lipoprotein;
20) squalane epoxidase inhibitors;
21) platelet aggregate inhibitors;
22) 5-lipoxygenase activated protein inhibitors such as MK-591 and the like.

The "remedy for hypertension" include, for example, the following:
1) thiazide diuretics such as chlorothialidon, chlorothiazide, dichlorofenamide, hydrofluorothiazide indapamide, hydrochlorothiazide and the like; loop diuretics such as bumetanide, ethacrynic acid, furosemide, torsemide and the like; sodium diuretics such as amyloride, triamteren and the like; aldosterone antagonist diuretics such as spironolactone, epilenone and the like;
2) β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, probanolol, sotalol, tertatolol, tilisolol, timolol and the like;
3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil and the like;
4) angiotensin converting enzyme inhibitors such as benazepril, captopril, cilazapril, delapril, enalapril, fosinopril, imidapril, rosinopril, moexipril, quinapril, quinapril, ramipril, perindopril, perindropri, quanipril, spirapril, tenocapril, trandolapril, zofenopril and the like;
5) neutral endopeptidase inhibitors such as omapatrilat, cadoxatril, ecadotril, fosidotril, sampatrilat, AVE7688, ER4030 and the like;
6) endotheline antagonists such as tezosentan, A308165, YM62899 and the like;
7) vasodilators such as hydraladine, clonidine, minoxidil, nicotinyl alcohol and the like;
8) angiotensin II receptor antagonists such as candesartan, eporsartan, iribesartan, losartan, pratosartan, tasosartan, telmisartan, valsartan, EXP-3137, FI6828K, RNH6270 and the like;
9) α/β adrenalin blockers such as nipradilol, arotinolol, amoslalol and the like;
10) α 1 blockers such as terazosin, urapidil, purazosin, bunazosin, trimazosin, doxazosin, naphthopidil, indolamin, WHIP 164, XEN010 and the like;
11) α2 agonists such as lofexidine, tiamenidine, moxonidine, rilmenidine, guanobenz and the like; and
12) aldosterone inhibitors.

The "anti-obesity drugs" include, for example, the following:
1) 5HT (serotonin) transporter inhibitors such as paroxetine, fluoxetine, fenfluramine, fluvoxamine, sertraline, imiplamin and the like;
2) norepinephrine transporter inhibitors such as GW320659, desipramin, talsuprame, nomifensin and the like;
3) cannabinoid-1 receptor 1 (CB-1) antagonists/inverse-agonists such as Rimonabant (Sanofi Synthelabo), SR-147778 (Sanofi Synthelabo), BAY-65-2520 (Bayer), SLV-319 (Sorbei), as well as compounds disclosed in U.S. Pat. No. 5,532,237, U.S. Pat. No. 4,973,587, U.S. Pat. No. 5,013, 837, U.S. Pat. No. 5,081,122, U.S. Pat. No. 5,112,820, U.S. Pat. No. 5,292,736, U.S. Pat. No. 5,624,941, U.S. Pat. No. 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887 and EP-658546 and the like;
4) glerin antagonists such as compounds disclosed in WO01/87355, WO02/08250 and the like;
5) histamine(H3) antagonists/inverse-agonists such as thioperamide, 3-(1H-imidazol-4-yl)propyl N-(pentenyl)carbonate, clobenpropit, iodofenpropit, imoproxyfen, GT2395, A331440, compounds disclosed in WO02/15905, O-[3-(1H-imidazol-4-yl)propanol]carbamate, piperazine-containing H3-receptor antagonists (Lazewska, D. et al., *Pharmazie*, 56: 927-32 (2001)), benzophenone derivatives (Sasse, A. et al., *Arch. Pharm.* (Weinheim) 334: 45-52 (2001)), substituted N-phenylcarbamates (Reidemeister, S. et al., *Pharmazie*, 55: 83-6 (2000)), proxyfen derivatives (Sasse, A. et al., *J. Med. Chem.*, 43: 3335-43 (2000)) and the like;
6) MCH-1R antagonists such as T-226296 (Takeda), SNP-7941 (Synaptic), other compounds disclosed in WO01/82925, WO01/87834, WO02/051809, WO02/06245, WO02/076929, WO02/076947, WO02/04433, WO02/

51809, WO02/083134, WO02/094799, WO03/004027 and JP-A-2001-226269 and the like;
7) MCH-2R agonists/antagonists;
8) NPY1 antagonists such as isopropylester 3-chloro-5-(1-(6-[2-(5-ethyl-4-methyl-thiazol-2-yl)-ethyl]-4-morpholinyl-4-yl-pyridin-2-ylamino)-ethyl)phenyl]carbamate, BIBP3226, BIBO3304, LY-357897, CP-671906, GI-264879, and other compounds disclosed in U.S. Pat. No. 6,001,836, WO96/14307, WO01/23387, WO99/51600, WO01/85690, WO01/85098, WO01/85173 and WO01/89528 and the like;
9) NPY5 antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. No. 6,140,354, U.S. Pat. No. 6,191,160, U.S. Pat. No. 6,258,837, U.S. Pat. No. 6,313,298, U.S. Pat. No. 6,337,332, U.S. Pat. No. 6,329,395, U.S. Pat. No. 340,683, U.S. Pat. No. 6,326,375, U.S. Pat. No. 6,329,395, U.S. Pat. No. 6,337,332, U.S. Pat. No. 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789, and compounds disclosed in Norman et al., *J. Med. Chem.*, 43:4288-4312 (2000) and the like;
10) leptins such as human recombinant leptin (PEG-OB, Hoffman La Roche), recombinant methionyl leptin (Amgen) and the like;
11) leptin derivatives such as compounds disclosed in U.S. Pat. No. 5,552,524, U.S. Pat. No. 5,552,523, U.S. Pat. No. 5,552,522, U.S. Pat. No. 5,521,283, WO96/23513, WO96/23514, WO96/23515, WO96/23516, WO96/23517, WO96/23518, WO96/23519, WO96/23520 and the like;
12) opioid antagonists such as nalmefen (Revex®), 3-methoxynaltrexone, naloxon, naltrexone, compounds disclosed in WO00/21509 and the like;
13) orexin antagonists such as SB-334867A, and other compounds disclosed in WO01/96302, WO01/68609, WO02/51232, WO02/51838 and WO03/023561 and the like;
14) bombesin receptor subtype-3 agonists;
15) cholecystokinin A (CCK-A) agonists such as AR-R15849, GI-181771, JMV-180, A-71378, A-71623, SR-146131, and other compounds disclosed in U.S. Pat. No. 5,739,106 and the like;
16) CNTF (ciliary neurotrophic factors) such as GI-181771 (Glaxo-Smith Kline), SR146131 (Sanofi Synthelabo), butabindide, PD170,292, PD149164 (Pfizer) and the like;
17) CNTF derivatives such as axokine (Regeneron), and other compounds disclosed in WO94/09134, WO98/22128, WO99/43813 and the like;
18) growth hormone secretion receptor agonists such as NN703, hexarelin, MK-0677, SM-130686, CP-424,391, L-692,429, L-163,255, and compounds disclosed in U.S. Pat. No. 6,358,951, US Patent Application Nos. 2002/049196, 2002/022637, WO01/56592, WO02/32888 and the like;
19) serotonin receptor-2C agonists such as BVT933, DPCA37215, IK264, PNU22394, WAY161503, R-1065, YM348, and other compounds disclosed in U.S. Pat. No. 3,914,250, WO02/36596, WO02/48124, WO02/10169, WO01/66548, WO02/44152, WO02/51844, WO02/40456 and WO02/40457 and the like;
20) melanocortin-3 receptor agonists;
21) melanocortin-4 receptor agonists such as CHIR86036 (Chiron), ME-10142, ME-10145 (Melacure), and other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949 and WO03/009847 and the like;
22) monoamine re-absorption inhibitors such as sibutramine (Meridia®/Reductil®) and its salts, and other derivatives disclosed in U.S. Pat. No. 4,746,680, U.S. Pat. No. 4,806,570, U.S. Pat. No. 5,436,272, US Patent Application No. 2002/0006964, WO01/27068, WO01/62341 and the like;
23) serotonin re-uptake inhibitors such as dexfenfluramine, fluoxetine, and other compounds disclosed in U.S. Pat. No. 6,365,633, WO01/27060 and WO01/162341;
24) glucagon-like peptide-1 agonists;
25) Topiramate (Topimax®);
26) phytopharm compound 57 (e.g., CP644,673);
27) acetyl CoA carboxylase-2 (ACC2) inhibitors;
28) β adrenalin receptor-3 agonists such as AD9677/TAK677 (Dai-Nippon Pharmaceutical/Takeda Chemical), CL-316,243, SB418790, BRL-37344, L-796568, BMS-196085, BRL-35135A, CGP12177A, BTA-243, W427353, Trecadrine, Zeneca D7114, SR59119A, and other compounds disclosed in U.S. Pat. No. 5,705,515, U.S. Pat. No. 5,451,677, WO01/74782 and WO02/32897;
29) diacylglycerol acyltransferase-1 inhibitors;
30) diacylglycerol acyltransferase-2 inhibitors,
31) fatty acid synthesis inhibitors such as Carulenin, C75 and the like;
32) phosphodiesterase inhibitors such as theophylline, pentoxifylline, zaprinast, sildenafil, amrinone, milrinone, cilostamide, rolipram, cilomilast and the like;
33) thyroid hormone-β agonists such as KB-2611 (KaroBio BMS), and other compounds disclosed in WO02/15845, JP-A-2000-256190 and the like;
34) UCP (uncoupling protein)-1, 2, or 3 activators such as phytanic acid, 4-[(E)-2-(5,6,7,8-tetrahydro-5,5,8,8-tetramethyl-2-naphthalenyl)-1-propenyl]benzoic acid (TT-NPB), retinoic acid, and other compounds disclosed in WO99/00123 and the like;
35) acylestrogens such as oleoylestrone, and other compounds disclosed in del Mar-Grasa, M. et al., *Obesity Research*, 9:202-9 (2001) and the like,
36) glucocorticoid antagonists;
37) 11-β-hydroxysteroid dehydrogenase-1 inhibitors such as BVT3498, BVT2733, and other compounds disclosed in WO01/90091, WO01/90090, WO01/90092 and the like;
38) stearoyl-CoA desaturase-1 inhibitors;
39) dipeptidyl peptidase-IV inhibitors such as isoleucine thiazolidide, valine pyrrolidide, NVP-DPP728, AF237, P93/01, TSL225, TMC-2A/2B/2C, FE999011, P9310/K364, VIP0177, SDZ274-444, and other compounds disclosed in WO03/004498, WO03/004496, EP1258476, WO02/083128, WO02/062764, WO03/000250, WO03/002530, WO03/002531, WO03/002553, WO03/002593, WO03/000180 and WO03/000181 and the like;
40) lipase inhibitors such as tetrahydroliptatin (orlistat/Xenical®), Triton WR1339, RHC80267, lipstatin, tea saponin, diethylumbelliferyl phosphate, FL-386, WAY-121898, Bay-N-3176, valilactone, esteracin, ebelactone A, ebelactone B, RHC80267, and disclosed in WO01/77094, U.S. Pat. No. 4,598,089, U.S. Pat. No. 4,452,813, U.S. Pat. No. 5,512,565, U.S. Pat. No. 5,391,571, U.S. Pat. No. 5,602,151, U.S. Pat. No. 4,405,644, U.S. Pat. No. 4,189,438 and U.S. Pat. No. 4,242,453 and the like;
41) fatty acid transporter inhibitors;
42) dicarboxylate transporter inhibitors;
43) glucose transporter inhibitors; or
44) phosphate transporter inhibitors and the like.

The above-mentioned combined pharmaceutical preparations may be prepared by combining the form I crystal of the invention and one or more of the above-mentioned co-drugs. The combined pharmaceutical preparations with one or more drugs selected from a group consisting of remedy for diabetes and remedy for hyperlipemia are useful for prevention or treatment of metabolic disorders. In particular, when the combined preparation with a remedy for hypertension and an anti-obesity drug is further combined with a remedy for diabetes and/or a remedy for hyperlipemia, then it is useful for prevention or treatment of metabolic disorders as having a synergistic effect of the constitutive ingredients.

When the form I crystal of the invention is used in clinical fields, then the dose and the administration frequency thereof may vary depending on the sex, the age, the body weight and the condition of the patient and on the type and the scope of the treatment of the patient. In oral administration, in general, the dose may be from 0.01 to 100 mg/kg-adult/day, preferably from 0.03 to 1 mg/kg-adult/day, and it may be administered all at a time or may be administered in a few times as divided into a few portions. In parenteral administration, its dose may be from 0.001 to 10 mg/kg-adult/day, preferably from 0.001 to 0.1 mg/kg-adult/day, and it may be administered all at a time or may be administered in a few times as divided into a few portions.

Ordinary physicians, veterinarians and clinicians may readily determine the effective dose necessary for retarding, inhibiting or stopping the development of diseases.

EXAMPLES

The invention is described more concretely with reference to the following Examples, which, however, do not whatsoever restrict the invention.

For thin-layer chromatography of the compounds in the Examples, used was a plate of Silicagel 60F$_{245}$ (Merck); and for detection, used was a UV detector. Wakogel™ C-300 (Wako Pure Chemicals) was used for a column silica gel; and LC-SORB™ SP-B-ODS (Chemco) or YMC-GEL™ ODS-AQ 120-S50 (Yamamura Chemical Laboratories) was for a reversed-phase column silica gel. Mass spectrum was measured according to an electrospray ionization (ESI) process, using QuattroII (Micromass). In NMR spectrometry, dimethyl sulfoxide was used for the internal standard in measurement in a heavy dimethyl sulfoxide solution. Using a spectrometer of Gemini-200 (200 MHz; Varian), Gemini-300 (300 MHz; Varian), Mercury 400 (400 MHz; Varian) or Inova 400 (400 MHz; Varian), each sample was analyzed for the total $\delta$ value in ppm.

CDCl$_3$: heavy chloroform
CD$_3$OD: heavy methanol
DMSO-d$_6$: heavy dimethyl sulfoxide The meanings of the abbreviations in nuclear magnetic resonance spectrometry are mentioned below.
s: singlet
d: doublet
dd: double-doublet
t: triplet
m: multiplet
br: broad
q: quartet
J: coupling constant
Hz: hertz

Compound 1 (30 g) was suspended in acetic anhydride (150 mL), and stirred at room temperature for 5 hours and then for 2 hours after heated up to 80° C. after cooling to room temperature, the solvent was evaporated off under reduced pressure. Diisopropyl ether (200 mL) and heptane (50 mL) were added to the obtained pale yellow solid, and stirred for 1 hour while intermittently ultrasonicated. The precipitate was taken out through filtration, washed with a small amount of diisopropyl ether, and then dried under reduced pressure to obtain a compound 2 (22.6 g, yield 85%) as a white solid.

$^1$HNMR (400 MHz, CDCl$_3$, δ ppm): 2.49 (3H, s), 7.76 (1H, dd, J=7.3, 2.0 Hz), 7.84-7.91 (2H, m).

Potassium carbonate (269 g) and pyrrolidine (200 mL) were added in that order to a THF solution (500 mL) of 3-bromopropanol (200 g) at 0° C. The reaction liquid was stirred at room temperature for 15 hours, then ethyl acetate (500 mL) was added to it, and further stirred at room temperature for 1 hour. The obtained reaction liquid was filtered through Celite, and the solid on the Celite was washed with ethyl acetate. The wash liquid and the filtrate were concentrated under reduced pressure, and ethyl acetate (500 mL) was added to the resulting residue, then stirred for 1 hour and filtered through Celite. The filtrate was concentrated under reduced pressure, and the resulting residue was purified through distillation (boiling point: 62° C., 1 mmHg) to obtain (3-hydroxypropyl)pyrrolidine (156 g, yield 95%).

$^1$HNMR (400 MHz, CDCl$_3$, δ ppm): 1.69-1.78 (6H, m), 2.53-2.59 (4H, m), 2.73 (2H, t, J=5.6 Hz), 3.81 (2H, t, J=5.4 Hz), 5.58 (1H, brs)

A DMF solution (200 mL) of (3-hydroxypropyl)pyrrolidine (100 g) was dropwise added to a DMF (500 mL) suspension of sodium hydride (43.2 g, 60% oil dispersion), at 0° C. The reaction liquid was stirred at 0° C. for 10 minutes, then a DMF solution (200 mL) of 4-fluoronitrobenzene (109 g, 0.774 mol) was dropwise added to it, stirred at 0° C. for 1 hour and then at room temperature for 16 hours. The obtained reaction liquid was poured into water, and extracted with ethyl acetate. The organic layer was washed with saturated saline water, and dried with anhydrous magnesium sulfide, and the solvent was evaporated off under reduced pressure. The residue was purified through silica gel column chromatography (hexane/ethyl acetate=1/1 to chloroform/methanol=9/1 to 5/1) to obtain a compound 3 (155 g, yield 83%) as a yellow oily substance.

$^1$HNMR (400 MHz, CDCl$_3$, δ ppm): 1.77-1.82 (4H, m), 2.00-2.08 (2H, m), 2.50-2.54 (4H, m), 2.63 (2H, t, J=7.2 Hz), 4.12 (2H, t, J=6.4 Hz), 6.94 (2H, d, J=9.6 Hz), 8.17 (2H, d, J=9.6 z).

10% Pd/C (21 g) and p-toluenesulfonic acid monohydrate (76 g) were added to a methanol solution (200 mL) of the compound 3 (50 g), and vigorously stirred in a hydrogen atmosphere for 45 hours. The reaction liquid was filtered through Celite, and the filtrate was concentrated under reduced pressure. With stirring, ethyl acetate (1000 mL) was dropwise added to an ethanol solution (50 mL) of the obtained pale pink oily substance, and stirred for 1 hour. The resulting precipitate was taken out through filtration, and dried under reduced pressure to obtain a compound 4 (91.2 g, yield 81%) as a white solid.

$^1$H-NMR (DMSO-d$_6$) δ: 1.81-1.90 (2H, m), 1.96-2.05 (2H, m), 2.06-2.13 (2H, m), 2.29 (6H, s), 3.02-3.04 (2H, m), 3.28-3.30 (2H, m), 3.57-3.59 (2H, m), 4.05 (2H, t, J=6.1 Hz), 7.03 (2H, d, J=8.8 Hz), 7.12 (4H, d, J=7.8 Hz), 7.28 (2H, d, J=8.8 Hz), 7.49 (4H, d, J=7.8 Hz), 9.49 (1H, brs), 9.73 (2H, brs).

The compound 2 (12.5 g) and the compound 4 (25.63 g) were suspended in glacial acetic acid (100 mL), and stirred in a nitrogen atmosphere at room temperature for 2 hours, and then the compound 2 (4.15 g) was further added thereto, and stirred for 3 hours. Further, the compound 2 (4.15 g) was added to it, and stirred at room temperature for 1 hour, and then heated up to 50° C. and stirred for 20 hours. The solvent was evaporated off under reduced pressure, and the residue was diluted with ethyl acetate, poured into saturated citric acid solution (500 mL). The aqueous layer was washed with ethyl acetate (200 mL×3). The pH of the aqueous layer was adjusted to be 10 to 11 with aqueous 6 N sodium hydroxide solution, and then this was extracted with ethyl acetate (300 mL×2). The organic layer was washed with aqueous saturated ammonium chloride solution (200 mL×3) and saturated saline water (200 mL), then dried with anhydrous sodium sulfate, and the solvent was evaporated off under reduced pressure. The obtained white solid was dissolved in hot ethanol (40 mL) with stirring, and then left cooled to room temperature. Then, water (60 mL) was dropwise added to it, and stirred for 1 hour at room temperature. The resulting solid was taken out through filtration, washed with water, and dried under reduced pressure to obtain a compound 5 (10.8 g, yield 55%) as a colorless crystal (form I crystal of 2-methyl-3-{-4-[3-(1-pyrrolidinyl)propoxy]phenyl}-5-trifluoromethyl-4(3H)-quinazolinone).

$^1$HNMR (400 MHz, CDCl$_3$, δ ppm): 1.77-1.83 (4H, m), 2.00-2.08 (2l-1, m), 2.26 (3H, s), 2.51-2.57 (4H, m), 2.63 (2l-1, t, J=7.2 Hz), 4.07 (2H, t, J=6.8 Hz), 7.03 (2H, d, J=8.8 Hz), 7.12 (2H, d, J=8.8 Hz), 7.79 (1H, t, J=7.6 Hz), 7.82-7.88 (2H, m).

Using a full-automatic powdery X-ray diffraction meter X'pert PRO (2 kW) (manufactured by Spectris (PANalytical)), the form I crystal thus obtained in the manner as above was subjected to powdery X-ray diffractiometry. The test condition was as in Table 3, and the data obtained are shown in Table 4.

TABLE 3

| Scanning Axis | Goniometry |
| --- | --- |
| Start Position [° 2Th.] | 3.5080 |
| End Position [° 2Th.] | 39.9900 |
| Step Size [° 2Th.] | 0.0170 |
| Scanning Step Time [s] | 20.9550 |

TABLE 3-continued

| Scanning Axis | Goniometry |
|---|---|
| Scan Type | continuous |
| PSD Mode | scanning |
| PSD Distance [° 2Th.] | 2.13 |
| Offset [° 2Th.] | 0.0000 |
| Diffusion Slit (DS) Type | fixed |
| Diffusion Slit (DS) Size [°] | 0.2500 |
| Sample Width [mm] | 10.00 |
| Test Temperature [° C.] | 25.00 |
| Target | Cu |
| X-ray Output Set | 45 kV, 40 mA |
| Goniometer Radius [mm] | 240.00 |
| Focus-DS Distance [mm] | 100.00 |
| Incident Side Monochrometer | no |
| Spinner | yes |

TABLE 4

| 2θ | Relative Intensity [cps] |
|---|---|
| 6.4 | 100.0 |
| 9.7 | 34.0 |
| 10.2 | 2.1 |
| 12.9 | 10.3 |
| 14.2 | 2.5 |
| 14.7 | 14.5 |
| 16.0 | 4.9 |
| 16.3 | 4.4 |
| 16.8 | 2.0 |
| 17.6 | 1.9 |
| 19.5 | 13.2 |
| 20.3 | 37.8 |
| 20.6 | 25.3 |
| 21.2 | 9.1 |
| 21.8 | 0.7 |
| 22.1 | 4.4 |
| 22.4 | 2.6 |
| 22.6 | 1.7 |
| 24.0 | 4.4 |
| 24.3 | 4.9 |
| 24.9 | 1.0 |
| 25.7 | 1.8 |
| 25.9 | 2.6 |
| 26.5 | 2.5 |
| 26.7 | 8.6 |
| 27.4 | 1.6 |
| 29.1 | 1.8 |
| 29.4 | 1.5 |
| 32.3 | 1.6 |
| 39.0 | 0.7 |

Note)
The intensity is a relative value based on the maximum, 100.

Pharmaceutical Test Examples of Form I Crystal

The usefulness of the form I crystal of the invention as a medicine was assessed according to the pharmaceutical test examples mentioned below.

Pharmaceutical Test Example 1

Histamine Analogue-Binding Inhibition Test

A cDNA sequence coding for a human histamine-3 receptor [see WO00/39164] was cloned with expression vectors pCR2.1, pEF1x (by Invitrogen) and pCI-neo (by Promega). The resulting expression vector was transfected into host cells, HEK293 and CHO-K1 (American Type Culture Collection), according to a cationic lipid process [see *Proceedings of the National Academy of Sciences of the United States of America*, Vol., 84, p. 7413 (1987)] to obtain histamine-3 receptor expression cells.

A membrane specimen prepared from the cells having expressed a histamine-3 receptor was incubated in an assay buffer (50 mM Tris buffer, pH 7.4) along with a test compound and 20,000 cpm [$^3$H]N-α-methylhistamine (by NEN) therein, at 25° C. for 2 hours, and then filtered through a glass filter GF/C. After washed with 50 mM Tris buffer (pH 7.4), the radioactivity on the glass filter was determined. The non-specific binding was determined in the presence of 10 μM thioperamide (by Sigma), and the 50% inhibitory concentration ($IC_{50}$) of the test compound to the specific N-α-methylhistamine binding was calculated [see *Molecular Pharmacology*, Vol. 55, p. 1101 (1999)]. As a result, $IC_{50}$ of the form I crystal of the invention was 2 nM.

As in the above, the form I crystal of the invention strongly inhibited the binding of N-alpha-methylhistamine, histamine analogue, to histamine-H3 receptor.

Pharmaceutical Test Example 2

Intracerebral Histamine Release Promotion Test

A histamine 3 receptor antagonist or inverse-agonist is reported to promote histamine release at the nerve end presynaptic region in a brain. For the purpose of investigating the effect of the medicine of the invention on these, a test compound suspended in an aqueous 0.5% methyl cellulose solution was orally administered to male SD rats (7 to 10-week age, 200 to 300 g) treated with a monoamine oxidase inhibitor (Pargyline). 2 hours after the medicine administration, the rats were killed in euthanasia, and the brain tissue was rapidly taken out. According to a Miyamoto et al's method, the concentration of histamine and its main metabolite, tele-methylhistamine in the brain tissue was measured [see *Analytical Biochemistry*, Vol. 334, p. 89 (2004)]. As a result, the form I crystal of the invention significantly increased the brain tele-methylhistamine level, at a dose of 30 mg/kg, and this indicates that the form I crystal promotes histamine release.

The compound of the invention acts as a substance having an effect of antagonizing histamine to bind to a histamine-H3 receptor or an activity of inhibiting the homeostatic activity that a histamine-H3 receptor has, or that is, a substance capable of effectively functioning as a histamine-H3 receptor antagonist or inverse-agonist when taken in living bodies; and it is useful for prevention or treatment of metabolic system disorders, circulatory system disorders or nervous system disorders.

The invention claimed is:

1. A form I crystal of 2-methyl-3-{4-[3-(1-pyrrolidinyl)propoxy]phenyl}-5-trifluoromethyl-4(3H)-quinazolinone.

2. The form I crystal of claim 1 which has X-ray powder diffraction peaks at diffraction angles (2θ±0.2°) of 6.4°, 9.7°, 20.3° and 20.6°.

3. The form I crystal of claim 1 which has X-ray powder diffraction peaks at diffraction angles (2θ±0.2°) of 6.4°, 9.7°, 12.9°, 14.7°, 19.5°, 20.3°, 20.6°, 21.2° and 26.7°.

4. The form I crystal of claim 1 which has X-ray powder diffraction peaks at diffraction angles (2θ±0.2°) of 6.4°, 9.7°, 10.2°, 12.9°, 14.2°, 14.7°, 16.0°, 16.3°, 16.8°, 17.6°, 19.5°, 20.3°, 20.6°, 21.2°, 21.8°, 22.1°, 22.4°, 22.6°, 24.0°, 24.3°, 24.9°, 25.7°, 25.9°, 26.5°, 26.7°, 27.4°, 29.1°, 29.4°, 32.3° and 39.0°.

Figure 1:
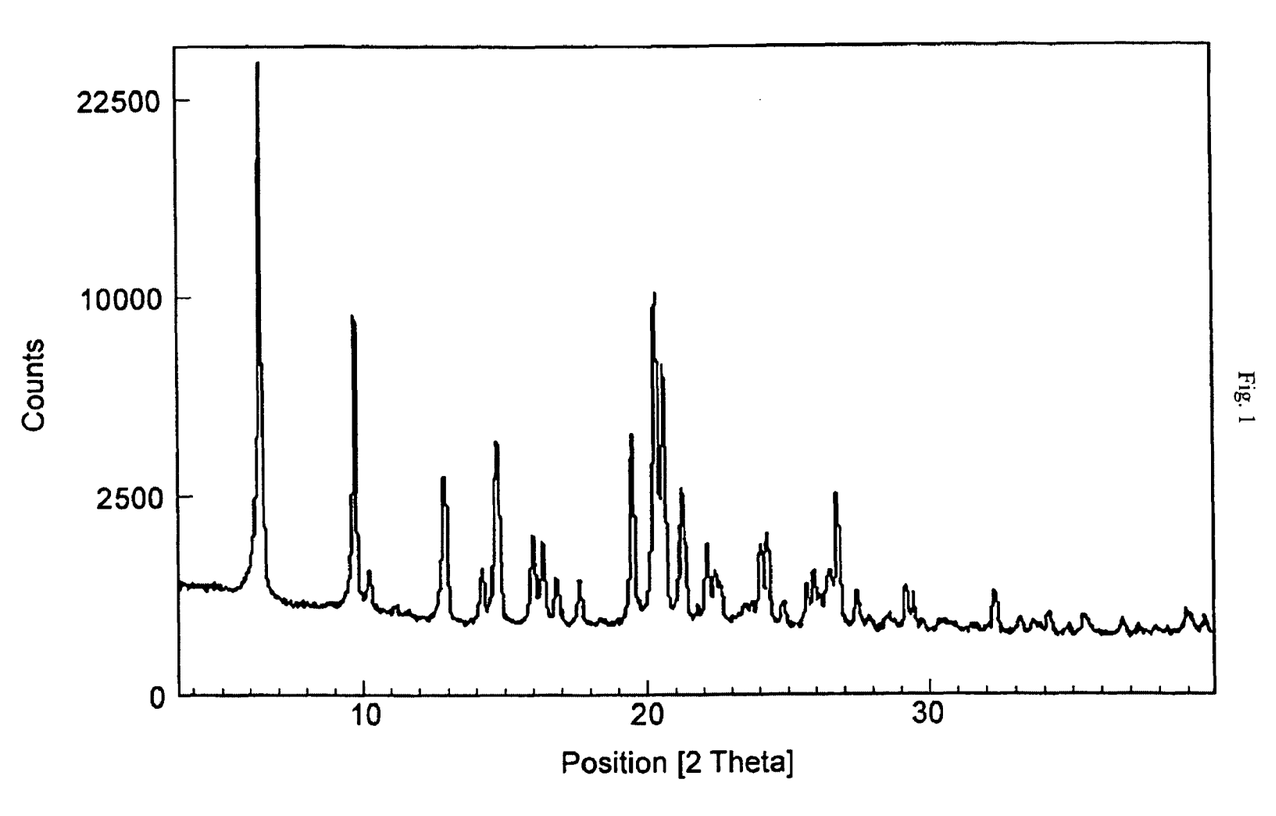
FIG. 1 shows a diffraction pattern of a form I crystal of 2-methyl-3-{4-{3-(1-pyrrolidinyl)propoxy]phenyl}-5-trifuromethyl-4(3H)-quinazolinone in powdery X-ray diffractiometry.

5. The form I crystal of claim 1 which has an X-ray powder diffraction pattern as shown in FIG. 1.

6. The form I crystal of claim 1 which has an endothermic peak at 141° C. in differential scanning calorimetry.

7. The form I crystal of claim 1 which is obtained by reacting the following compound (a) and the following compound (b) or its acid addition salt:

8. A pharmaceutical composition which comprises an inert carrier and the form I crystal of claim 1 or a pharmaceutically acceptable salt thereof.

9. A pharmaceutical composition which comprises an inert carrier and the form I crystal of claim 2 or a pharmaceutically acceptable salt thereof.

10. A pharmaceutical composition which comprises an inert carrier and the form I crystal of claim 3 or a pharmaceutically acceptable salt thereof.

11. A pharmaceutical composition which comprises an inert carrier and the form I crystal of claim 4 or a pharmaceutically acceptable salt thereof.

12. A pharmaceutical composition which comprises an inert carrier and the form I crystal of claim 5 or a pharmaceutically acceptable salt thereof.

13. A pharmaceutical composition which comprises an inert carrier and the form I crystal of claim 6 or a pharmaceutically acceptable salt thereof.

* * * * *